US00PP10444P

United States Patent [19]

Lemon

[11] Patent Number: Plant 10,444

[45] Date of Patent: Jun. 9, 1998

[54] VARIETY OF GERANIUM PLANT NAMED 'HELENA'

[75] Inventor: David Lemon, Lompoc, Calif.

[73] Assignee: John Bodger & Sons Company, So. El Monte, Calif.

[21] Appl. No.: 724,677

[22] Filed: Oct. 1, 1996

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 7,358 10/1990 Guillou et al. ..... Plt./87.12

P.P. 7,720 11/1991 Guillou et al. ..... Plt./87.12

*Primary Examiner*—Howard J. Locker

*Attorney, Agent, or Firm*—Fulwider Patton Lee & Utecht, LLP

[57] ABSTRACT

The cultivar is characterized by the bright pink flower color and a distinctive zone on medium green foliage. Its quick rooting time and continuous flowering provides for superb cuttings and for quick recovery of the bloom following wet weather conditions. The cultivar provides a relatively large floret, and an abundant amount of cuttings may be obtained from a single plant.

1 Drawing Sheet

BACKGROUND OF THE INVENTION

The present invention comprises a new and distinct cultivar of *Pelargonium×peltatum* known by the varietal name Helena (Oglevee No. 3148, Bodger No. 2GM 213-8). The new variety was discovered in a selective breeding program by David Lemon at Bodger Seeds, Ltd., Lompoc, Calif. The new variety is a selection from the crossing of Nicole (U.S. Plant Pat. No. 7,358) which has early blooming, candy pink flowers and medium green leaves having a very dark zone, with Monique (U.S. Plant Pat. No. 7,720) which has dark candy pink flowers and medium dark leaves having a medium zone, as compared with the claimed cultivar which has bright pink flowers and medium green leaves having a small and distinct zone.

The new cultivar was first asexually reproduced by cuttings at Oglevee Ltd., Connellsville, Pa. and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa. using full light, 60° Fahrenheit night temperature, 68° Fahrenheit day temperature, 72° Fahrenheit vent temperature and grown in a soilless media of constant fertilizer 200–250 parts per million of nitrogen and potassium has a response time of six weeks from the rooted cutting to a flowering plant in a 10.0 cm pot.

DESCRIPTION OF THE DRAWING

The accompanying drawing illustrates primarily the florets of the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted on approximately Feb., 1, 1996 and flowering on approximately Mar. 14, 1996 under full light and greenhouse, and colorings were taken indoors under 200–220 foot candles of fluorescent cool white light using the R.H.S. Colour Chart of The Royal Horticultural Society of London.

The Plant

Classification:

*Botanical.*—*Pelargonium×peltatum.*

*Commercial.*—Ivy Geranium Helena.

Form: Cascading mound.

*Height.*—28–30 cm from media surface.

*Growth.*—Free branching; upright mound with cascading side growth.

*Strength.*—Upright mound needing no support while outer branches cascade.

Foliage: Stalked leaf attachment with dark central zone; slightly reflective; pubescence reduces shine.

Leaves:

*Size.*—8.5–9.5 cm when filly expanded.

*Shape.*—Reniform with cordate base.

*Margin.*—Pedately lobed.

*Texture.*—Leathery but slightly pubescent.

*Color.*—Top: Green group 137C. Bottom: Yellow-green group 147B. Zone: Brown group 200A.

*Ribs and veins.*—Palmate venation: Color: Yellow-green group 146C.

Petioles:

*Length.*—5.5–9.5 cm.

*Color.*—Yellow-green group 146B.

Stem:

*Color.*—Yellow-green group 146B.

*Internodes.*—4.0 cm–5.5 cm.

The Bud (Umbel)

Shape: Elliptical; cluster.

Size: 5.5–7.0 cm across.

Inflorescence

Blooming habit: Continuous; free and early flowering.

Borne: Florets on pedicel; pedicel on peduncle; 12.0–14.0 cm above foliage.

Closed florets:

*Bud size.*—Just cracking color, 1.5×1.0 cm.

*Size.*—Fully open bloom: 10–10.5 cm across; The florets are held closely in the inflorescence to produce a very dense show of color in a relatively small area.

Open florets:

*Form.*—Upper 5 petals open flat; lower petals stack to give a slight cupped appearance. Semi-double; overall color: top Red-Purple Group 58C, two to three petals have distinct eye of dark red-purple surrounding a lighter color flecked with red-purple. There are about 8 florets per inflorescence present.

*Color.*—Top: the overall appearance of the flower from a distance is 61D Red-purple group; there is gradation of color from the center of the floret appearing as 49A Red group, to the outer edge of the petal appearing as 55A Red group. Bottom: Veined with Red-purple group 61C. Eye: Red-purple group 61 B at outer margin of eye; vein with Red-purple group 61A; inner eye color is Red-purple group 62D.

*Petals.*—5 in number.

*Size.*—5.5–6.3 cm.

*Texture and appearance.*—Smooth, satiny looking, prominent eye appears on two of the petals.

Petaloids:

*Quantity.*—2–5 petaloids, the number of petaloids will vary throughout the season depending upon plant maturity and cultural conditions.

*Shape.*—Irregular; twisted; folded. Feathery, long and thin.

*Color.*—Top: Red-purple group 61D. Bottom: Red-purple group 61C; Red groups 55A and 49A.

Pedicel:

*Length.*—3.5–3.8 cm.

*Color.*—Yellow-green group 146C.

Peduncle:

*Length.*—20–21 cm.

*Color.*—Yellow-green group 146C.

Persistence:

*Disease resistance.*—Not known.

*Lasting quality.*—Unknown.

Reproductive Organs

Stamens:

*Anthers.*—Length: 2.5 mm.

*Filaments.*—Length: 0.8–1.0 cm. Color: White with a blush of petal color.

*Pollen.*—Golden brown.

Pistils:

*Number.*—5.

*Length.*—8.5–9.0 mm.

*Stigma.*—Color: Dark red.

*Style.*—Length: 5 mm.

Ovaries:

*Color.*—Green, superior, pubescent.

*Length.*—3.5 mm–4.0 mm.

Fruit: None.

General Characteristics

Helena is a new long trailing ivy geranium with a bright pink flower color and a distinct zone on medium green foliage. Improved qualities are a larger floret, quicker and easier rooting, increased cutting production and faster finishing time.

I claim:

1. A new and distinct variety of Geranium plant, substantially as shown and described.

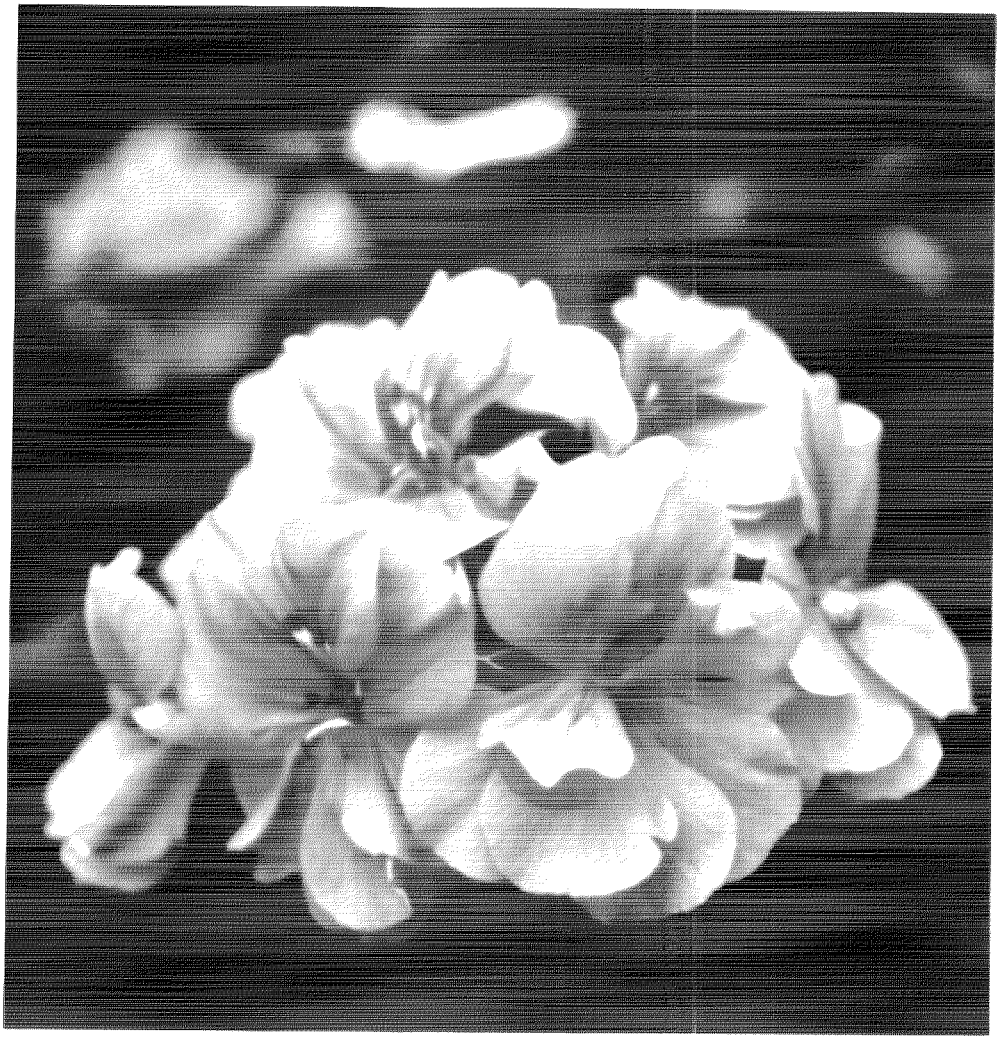

* * * * *